US010156537B2

(12) United States Patent
Hoffmann et al.

(10) Patent No.: US 10,156,537 B2
(45) Date of Patent: Dec. 18, 2018

(54) SENSOR FOR DETECTING A LIQUID IN A FLUID CHANNEL

(71) Applicant: FRAUNHOFER-GESELLSCHAFT ZUR FÖRDERUNG DER ANGEWANDTEN FORSCHUNG E.V., München (DE)

(72) Inventors: Almuth Hoffmann, Mainz (DE); Michael Bassler, Mainz (DE); Karin Potje-Kamloth, Neubiberg (DE); Knut Welzel, Wackernheim (DE); Matthias Besold, Mainz (DE)

(73) Assignee: FRAUNHOFER-GESELLSCHAFT ZUR FÖRDERUNG DER ANGEWANDTEN FORSCHUNG E.V., München (DE)

( * ) Notice: Subject to any disclaimer, the term of this patent is extended or adjusted under 35 U.S.C. 154(b) by 0 days.

(21) Appl. No.: 15/326,171

(22) PCT Filed: Jul. 16, 2015

(86) PCT No.: PCT/EP2015/066232
§ 371 (c)(1),
(2) Date: Jan. 13, 2017

(87) PCT Pub. No.: WO2016/008962
PCT Pub. Date: Jan. 21, 2016

(65) Prior Publication Data
US 2017/0205369 A1     Jul. 20, 2017

(30) Foreign Application Priority Data
Jul. 18, 2014   (DE) .................. 10 2014 214 026

(51) Int. Cl.
*G01N 27/447* (2006.01)
*G01N 27/22* (2006.01)
(Continued)

(52) U.S. Cl.
CPC .......... *G01N 27/221* (2013.01); *B01L 3/5027* (2013.01); *G01N 27/4473* (2013.01);
(Continued)

(58) Field of Classification Search
CPC ...... G01R 27/08; G01R 27/22; G01R 27/228; G01N 27/07; G01N 27/22; G01N 27/221;
(Continued)

(56) References Cited

U.S. PATENT DOCUMENTS 3,826,979 A   7/1974 Steinmann
4,752,727 A   6/1988 Schneider
(Continued)

FOREIGN PATENT DOCUMENTS

DE   2239359 A1   2/1974
DE   3302736 A1   8/1984
(Continued)

OTHER PUBLICATIONS

Petkovic-Duran et al., "Detection of Inorganic Ions on a Capillary Electrophoresis Microchip Using a Conductivity Technique", Biomedical Applications of Micro- and Nanoengineering III, Proc. of SPIE, 2006, 6 pages, vol. 6416, 64160J.
(Continued)

*Primary Examiner* — Son Le
(74) *Attorney, Agent, or Firm* — Hudak, Shunk & Farine Co., LPA (57) ABSTRACT

A sensor for detecting a liquid in a fluid channel of a microfluidic component and to a microfluidic component having such a sensor. The sensor includes an electrode arrangement having a transmitting electrode, a receiving electrode and a first shielding electrode, which are arranged in a coplanar manner on a plane and can be positioned above or below, adjacent to the fluid channel, wherein the transmitting electrode and the receiving electrode are capaci-
(Continued)

tively coupled in that they each have an adjacently arranged edge having a dielectric therebetween. A method for detecting a liquid in a fluid channel of a microfluidic component having the steps: applying an alternating voltage to the transmitting electrode, coupling the alternating voltage into the receiving electrode, tapping an alternating current or alternating voltage signal on the receiving electrode, extracting extreme values from the tapped alternating current or alternating voltage signal, and assigning the extreme values to the position of a liquid front.

23 Claims, 8 Drawing Sheets

(51) Int. Cl.
*B01L 3/00* (2006.01)
*G01N 30/64* (2006.01)

(52) U.S. Cl.
CPC .................. B01L 2300/0645 (2013.01); B01L 2300/0663 (2013.01); G01N 30/64 (2013.01)

(58) Field of Classification Search
CPC .. G01N 27/227; G01N 27/228; G01N 27/447; G01N 27/4473; G01N 27/27; G01N 27/30; G01N 33/0031; G01N 33/0034; G01N 27/301; B01L 3/00; B01L 3/5027; B01L 2300/0645
See application file for complete search history.

(56) References Cited

U.S. PATENT DOCUMENTS

| | | | |
|---|---|---|---|
| 6,491,805 B1 | 12/2002 | Gordon et al. | |
| 7,509,856 B1 | 3/2009 | Winkens et al. | |
| 8,489,341 B2 | 7/2013 | Brown | |
| 2008/0121045 A1 | 5/2008 | Cole et al. | |
| 2012/0160691 A1* | 6/2012 | Mahabadi | G01N 27/4473 |
| | | | 204/603 |
| 2013/0293246 A1 | 11/2013 | Pollack et al. | |

FOREIGN PATENT DOCUMENTS

| | | |
|---|---|---|
| DE | 3433148 A1 | 3/1986 |
| DE | 19949985 C2 | 8/2001 |
| DE | 10107439 A1 | 12/2001 |
| DE | 102009000529 A1 | 8/2010 |
| EP | 2306183 A1 | 4/2011 |
| WO | 9510040 A1 | 4/1995 |

OTHER PUBLICATIONS

Pavel Kubáň et al., "Evaluation of Microchip Capillary Electrophoresis with External Contactless Conductivity Detection for the Determination of Major Inorganic Ions and Lithium in Serum and Urine Samples", Lab Chip 2008, pp. 1829-1836, vol. 8, Royal Society of Chemistry.

Pavel Kubáň et al., "Ten Years of Axial Capacitively Coupled Contactless Conductivity Detection for CZE—a Review", Electrophoresis, 2009, pp. 176-188, vol. 30, Wiley-VCH Verlag GmbH & Co. KGaA, Weinheim, DE.

Jan Lichtenberg et al "A Microchip Electrophoresis System with Integrated In-plane ISR (D3) Electrodes for Contactless Conductivity Detection", Electrophoresis, 2002, pp. 3769-3780, vol. 23, Wiley-VCH Verlag GmbH & Co. KGaA, Weinheim, DE.

Guijt R M et al "Conductivity Detection for Conventional and Miniaturized Capillary ISR (04) Electrophoresis Systems", Electrophoresis, 2004, pp. 4032-4057, vol. 25 Wiley Interscience, Weinheim, DE.

* cited by examiner

I　II　III

SENSOR FOR DETECTING A LIQUID IN A FLUID CHANNEL

FIELD OF THE INVENTION

The invention relates to a sensor for detecting a liquid in a fluid channel of a microfluidic component, to a microfluidic component having a surface, a fluid channel running in the interior, substantially parallel to the surface, and such a sensor, and to a method for detecting a liquid in a fluid channel of such a microfluidic component.

Deviations of the channel geometry from a nominal value, for example due to manufacturing fluctuations, can lead to uncertainties regarding the position of the liquid front, that is to say the interface between the liquid and an adjoining medium, even if the parameters of a fluid flow in the channel are precisely known. Further potential sources of error are inaccuracies in the conveying volume of the pump. Furthermore, in the case of channels which have already been wetted or which have dried again, the problem of temporal variation of the capillary forces occurs. Therefore, in order to monitor processes taking place in fluidic systems, it may be necessary to check the advancement of the liquid front at defined positions along the fluid channel.

In principle, it is advantageous in such detection methods to use a contactless sensor which is thus not in direct electrical or mechanical contact with the liquid but rather can be attached outside of the fluid channel. Contactless detectors are known in the form of light barriers which couple light inward through a transparent substrate of the microfluidic component. Reference is made for example to the document DE 10 2009 000 529 A1, which discloses a microfluidic chip in which the pressure within the fluidic system is determined indirectly by measuring the liquid level in a dead end of a channel filled with a gas bubble. The liquid level, that is to say the interface between the liquid and the adjoining gas bubble, is read optically by coupling in a light beam and optionally detecting the weakening thereof in a transmission measurement or the change in the light reflected at the interface of the measurement channel in a reflection measurement. For automatically reading the pressure, it is proposed to insert the chip in a predetermined manner into a suitable operator device having a light source and a light sensor.

One fundamental difficulty which may arise in this measurement method is the precise positioning of the light source (or of a light conductor if present) and the sufficiently precise focusing of the light by means of optical elements. Another fundamental problem when optically reading a liquid level in a fluid channel arises due to the wetting of the channels. A channel that has been wetted has different optical properties than a channel wall that has not been wetted, so that signal differences cannot in all cases permit a clear conclusion as to whether the channel is filled with liquid or merely wetted. For example, an empty channel may incorrectly be interpreted as full, or vice versa. Furthermore, this detection method is limited to transparent substrates.

Besides optical detection, the capacitive reading of a fill level of a medium in a container having a non-metal container wall is also known from other technical fields. Reference is made for example to the document DE 199 49 985 C2. The fill level sensor described therein comprises inter alia a capacitance consisting of two adjacent electrodes on the container wall, which represents a capacitive feedback of a connected amplifier. At the same time, one of the electrodes forms a further capacitance relative to ground, which is varied by the fill level in the container. The circuitry of the detector is such that the amplifier, on account of the capacitive feedback, oscillates only when the fill level of the medium in the container and thus the first capacitance is below a predetermined threshold.

Methods for the capacitive determination of constituents in a liquid in a fluid channel through which a flow is passing, in particular in a microfluidic system, are known from the field of capillary electrophoresis. In this regard, reference is made for example to the following three articles:

"Detection of inorganic ions on a capillary electrophoresis microchip using a conductivity technique", Petkovic-Duran et al., Proc. of SPIE Vol. 6416, 64160J, 2006;

"Evaluation of microchip capillary electrophoresis with external contact-less conductivity detection for the determination of major inorganic ions and lithium in serum and urine samples", Pavel Kubáň et al., Lab Chip, 2008, 8, 1829-1836;

"Ten years of axial capacitively coupled contactless conductivity detection for CZE—a review", Pavel Kubáň et al., Electrophoresis 2009, 30, 176-188.

The capillary electrophoresis described therein is carried out using microfluidic systems in which two electrodes are arranged one behind the other along a fluid channel, wherein a Faraday shield which is perpendicular to the direction of the fluid channel is arranged between the electrodes in order to avoid a direct capacitive coupling between the electrodes. The capacitive coupling should therefore—at least in theory—take place exclusively via the liquid located in the fluid channel, wherein the measurement with regard to a detection of different ions in the liquid requires a very high degree of sensitivity.

An overview of capacitive conductivity determination in capillary electrophoresis is given in the article "Conductivity detection for conventional and miniaturised capillary electrophoresis systems", Rosanne M. Guijt et al., Electrophoresis 2004, 25, 4032-4057. Inter alia, arrangements with and without a shielding electrode perpendicular to the fluid channel are examined in said article.

The coplanar arrangement of electrodes, including shielding electrodes, on a glass substrate of a chip for capillary electrophoresis for capacitive conductivity determination in fluids is also discussed in the article "A microchip electrophoresis system with integrated in-plane electrodes for contactless conductivity detection", Jan Lichtenberg et al., Electrophoresis 2002, 23, 3769-3780.

Classified in the same field is the document DE 101 07 439 A1, from which there is known a sample analysis system having a detector for detecting sample components moving along a channel. The detector comprises a detection electrode, which is capacitively coupled to the channel, and a first and a second driver electrode, wherein the first driver electrode is electrically coupled to the detection electrode through the channel.

The application WO 95/10040 A1 relates generally to an electrochemical detector for analyzing a flowing fluid in a fluid channel with up to 8 microelectrodes along the fluid channel.

Other methods for the capacitive determination of inhomogeneities or changes in liquids or for determining flow rates of a multiphase fluid in a fluid channel are known from the documents US 2008/0121045 A1, DE 34 33 148 A1 or DE 33 02 736 A1. The document DE 2 239 359 A relates to a capacitive moisture detector. The document US 2013/0293246 A1 describes a method for the capacitive determination of a droplet in a droplet actuator. The document U.S.

Pat. No. 8,489,341 B2 relates to a method for determining the composition of a liquid by means of a capacitor arrangement.

SUMMARY OF THE INVENTION

In contrast, the object of the present invention is to provide a sensor, a microfluidic component and a method for detecting a liquid in a fluid channel of a microfluidic component, which easily enables an extremely reliable detection of the liquid regardless of the nature thereof and any wetting of the fluid channel.

The object is achieved on the one hand by a sensor for detecting a liquid in a fluid channel of a microfluidic component, which comprises an electrode arrangement having a transmitting electrode, a receiving electrode and a first shielding electrode, which are arranged in a coplanar manner on a plane and can be positioned parallel to the fluid channel and above or below adjacent to the fluid channel, wherein the transmitting electrode and the receiving electrode are capacitively coupled in that they each have an adjacently arranged edge with a dielectric located therebetween.

On the other hand, the object is achieved by a method for detecting a liquid in a fluid channel of a microfluidic component takes place by means of an electrode arrangement having a transmitting electrode, a receiving electrode and a first shielding electrode, which are arranged in a coplanar manner on a plane substantially parallel to the fluid channel and above or below adjacent to the fluid channel, wherein the transmitting electrode and the receiving electrode each have an adjacently arranged edge with a dielectric located therebetween, and comprises the steps:

- applying an alternating voltage to the transmitting electrode,
- coupling the alternating voltage into the receiving electrode,
- tapping an alternating current signal or alternating voltage signal on the receiving electrode,
- extracting extreme values from the tapped alternating current signal or alternating voltage signal,
- assigning the extreme values to the position of a liquid front.

Definitions of terms will follow: in the context of this document, a "microfluidic component" will be understood to mean a component which is usually flat, typically in the credit card format, in particular a microfluidic chip, the baseplate (also called substrate) of which is made in particular of a polymer material, glass or silicon, in which the fluid channel or a plurality of fluid channels is formed in a manner known per se by injection molding, hot stamping or milling. In addition to the fluid channel, other microstructures may also be provided on or in the microfluidic component, such as for example micropumps, actuators, sensors, membranes, valves, stirring elements or the like.

In the context of this document, the term "fluid channel" refers to any types of cavities for guiding or storing fluid samples, in particular channels or microchannels but also other cavities in the component in which the fluid sample can be for example stored or subjected to a mechanical, thermal or chemical or biological process. Preferably, the fluid channel is formed by a groove in the baseplate, which on its upper side is closed against the surrounding environment by means of a cover.

The microfluidic component, sometimes also referred to as "lab-on-a-chip", can in general be used for chemical synthesis or analysis and also for medical diagnostics in the laboratory or on site. Due to the miniaturization, it is particularly suitable for the synthesis and/or analysis of extremely small substrate quantities. This often involves a very highly controlled throughflow of the fluid sample and a precise determination of the position of liquid fronts and of pressure conditions in the fluid line or the system of fluid lines in the component.

The term "transmitting electrode" denotes that electrode which is provided for connection to an alternating voltage source. In a corresponding manner, the term "receiving electrode" denotes that one of the electrodes which is provided for connection to an alternating current measuring device or alternating voltage measuring device. The "shielding electrode" is in principle passive and to this end will be pulled to a fixed potential, preferably to ground potential.

Like the capillary electrophoresis described above, the invention serves for the capacitive detection of a liquid, but unlike in the case of capillary electrophoresis there is no knowledge about any ions in the liquid, but rather only the presence of the liquid and in particular of the liquid front is to be detected. Therefore, unlike the above-described detection of inorganic ions, no shielding is provided between the transmitting electrode and the receiving electrode. Instead, these electrodes are directly capacitively coupled to one another. Directly coupled means that the electric field can propagate between the transmitting electrode and the receiving electrode directly via the ambient air, the dielectric substrate of the microfluidic component, to the surface of which the electrodes are attached, and optionally the liquid arriving in the fluid channel, depending on the permeability of the individual media, and in a manner that is not disrupted by a Faraday shield.

Accordingly, the shielding does not serve to prevent the direct coupling between the transmitting electrode and receiving electrode, but rather for amplifying the signal when passing a liquid front. The local change in the total permittivity through the passing liquid leads to a field change which, by virtue of a targeted geometric arrangement of the first shielding electrode, is amplified or spatially limited in such a way that the signal enables more accurate information to be obtained about the location of the liquid front, as will be explained in greater detail below on the basis of examples.

In terms of the method, the detection involves, besides a tapping of an alternating current signal or alternating voltage signal on the receiving electrode, also the subsequent extraction of extreme values from the tapped alternating current signal or alternating voltage signal and finally the assignment of the extreme values to the position of a liquid front. Depending on the geometric arrangement of the electrodes, one extreme value or in particular a plurality of extreme values may be detected, as a result of which the knowledge about the position of the liquid front is improved.

The sensor according to the invention has a simple design and can therefore in one advantageous embodiment of the invention be integrated in a simple and space-saving manner in an operator device. For measuring purposes, the microfluidic component need only be positioned with its surface, which runs parallel to the fluid channel, adjacent to the electrode arrangement of the external sensor in the operator device. When doing so, it must be ensured, for example by means of stop elements, that the relevant fluid channel comes to lie in a suitable position adjacent to the electrode arrangement having the transmitting electrode, the receiving electrode and the first shielding electrode. This aspect of the invention is referred to as the "external sensor", reference being made to the arrangement of the sensor relative to the microfluidic component.

According to the invention, the transmitting electrode and the receiving electrode of the sensor each have an adjacently arranged edge with a dielectric located therebetween.

This means that only material with dielectric properties, and not an electrical conductor, is arranged between the two adjacently arranged edges. In the case of the above-described arrangement of the microfluidic component in an operator device, usually air, the substrate material of the microfluidic component and the circuit board material of the sensor on which the electrode arrangement is fixed are located as a dielectric between the electrodes. Ultimately, what is important is that in any event no electrically conductive substance is incorporated in the intermediate space between the electrodes.

With particular preference, the adjacently arranged edges run parallel to one another. This embodiment corresponds at least in theory to the arrangement of two plane-parallel plates of a plate capacitor.

In signal processing terms, given an optimal orientation, it makes no significant difference whether the adjacent edges during the measurement run in the direction of the fluid channel or are arranged perpendicular thereto. Surprisingly, the signal curve looks very similar in both cases at least in terms of its shape. In this regard, both arrangements are in principle considered to be an embodiment according to the invention. However, the perpendicular arrangement of the edges relative to the orientation of the fluid channel has proven to be preferred because this has a higher degree of tolerance in terms of position. The signal is much less sensitive to a slight lateral offset of the electrodes relative to the position of the fluid channel. Therefore, the method according to the invention provides that the adjacently arranged edges are preferably oriented substantially perpendicular to the fluid channel.

Furthermore, the first shielding electrode is capacitively coupled to the transmitting electrode or to the receiving electrode or particularly preferably to the transmitting electrode and the receiving electrode.

The latter scenario is particularly preferred because this generates a signal curve with two extremes, as already indicated above. The extremes can then be assigned to two positions of the liquid front, namely on the one hand when the liquid front in the fluid channel reaches the middle of the electrode pair of the transmitting electrode and receiving electrode, and on the other hand when it has arrived between the receiving/transmitting electrode and the first shielding electrode.

Particular preference is therefore given to a microfluidic component in which the first shielding electrode has at least two sections, of which, as viewed in a direction in the plane of the electrode arrangement, a first section is arranged in front of and a second section is arranged behind the transmitting electrode and the receiving electrode.

In one particularly preferred embodiment, this can be achieved in that the first shielding electrode at least partially and preferably completely frames the transmitting electrode and the receiving electrode.

In one advantageous further development of the method, it is therefore provided that the first shielding electrode has at least two sections, of which, as viewed in each case in the direction of the fluid channel, a first section is arranged in front of and the second section is arranged behind the transmitting electrode and the receiving electrode, wherein a speed of the liquid front is derived from at least two temporally successive extreme values.

The extraction of extreme values from the tapped alternating current signal or alternating voltage signal preferably takes place in a manner known per se by forming the derivation from the tapped signal and determining the zero crossings of the derivation, which usually leads to a more precise extreme value determination.

Preferably, the sensor is further developed in that a signal source is connected to the transmitting electrode, and in that a signal pickup is connected to the receiving electrode.

In this case, the signal source is preferably an alternating voltage source and the signal pickup is preferably designed to detect the curve of an alternating current signal or alternating voltage signal over time.

By analogy with the advantageous further development of the method, the sensor is preferably further developed in that the signal pickup is designed to extract at least one extreme value from the alternating current signal or alternating voltage signal and to output said extreme value(s).

In the simplest case and therefore preferably, the exciter signal is an alternating voltage of constant frequency and amplitude.

Preferably, an effective current or an effective voltage is determined from the alternating current signal/alternating voltage signal tapped on the receiving electrode, and said effective current or effective voltage is used for the extreme value determination.

It is also advantageous if the electrode arrangement has a second shielding electrode arranged parallel to and at a distance from the plane.

By virtue of such a shielding of the transmitting and receiving electrodes on the rear side, the signal can be further improved. Said rear shielding limits the sensitive area of the sensor to the intermediate space between the plane formed by the transmitting electrode, receiving electrode and first shielding electrode and the plane of the second shielding electrode, and thus increases the sensitivity for permittivity changes taking place there.

If the transmitting electrode, receiving electrode and first shielding electrode are attached for example to a surface of a printed circuit board (PCB), the second shielding electrode is easily and therefore preferably arranged on the opposite surface of the printed circuit board and particularly preferably approximately in congruence with the transmitting electrode, receiving electrode and first shielding electrode.

As an alternative to the above-described use of the external sensor according to the invention in an operator device, the object is also achieved by a microfluidic component, which has a surface, a fluid channel running in the interior, substantially parallel to the surface, and a sensor as described above, wherein the transmitting electrode, the receiving electrode and the first shielding electrode are arranged in a coplanar manner on the surface and above or below adjacent to the fluid channel.

The sensor can thus also be designed as an element connected to the microfluidic component. In this aspect of the invention, use is made of the term "integrated sensor", which once again refers to the arrangement of the sensor relative to the microfluidic component.

All transmitting, receiving and shielding electrodes of the microfluidic component according to the invention can easily be applied to the surface(s) thereof. All types of metal coating are preferably suitable for this. Particular preference is given to laminated-on or glued-on films, the application of a liquid conductive lacquer or of a paste-like conductive substance (conductive paste) with subsequent drying or curing, the vapor deposition or electrolytic deposition of a metal or metal-containing coating. Alternatively, other metal bodies can also be mechanically or adhesively attached to the surface of the microfluidic component.

For the reasons given above, it is particularly preferred that the adjacently arranged edges of the transmitting and receiving electrodes on the surface of the microfluidic component are oriented substantially perpendicular to the fluid channel.

The transmitting, receiving and first shielding electrodes can be attached directly to the surface of the substrate or of the baseplate of the microfluidic component, that is to say the underside thereof, in which the fluid line is formed in the manner described above. However, they are particularly preferably located on the upper side which is formed by the cover, since the cover is usually a much thinner film and therefore a smaller distance between the electrode arrangement and the fluid channel can be achieved, which in turn increases the measurement accuracy, as will be demonstrated below.

The transmitting electrode, receiving electrode and first shielding electrode of the electrode arrangement are therefore preferably arranged at a distance of 500 µm or less, and particularly preferably 100 µm or less, from the fluid channel.

Analogously, in the method according to the invention using an external sensor, the microfluidic component is preferably placed in the operator device with its upper side, which is formed by the cover, adjacent to the electrode arrangement.

In the microfluidic component having an integrated sensor, the first shielding electrode is preferably arranged adjacent to the transmitting electrode or to the receiving electrode or to the transmitting electrode and the receiving electrode and spans the fluid channel at least once. If the first shielding electrode has at least two sections, as described above, said sections are preferably arranged in front of and behind the transmitting electrode and the receiving electrode, as viewed in the direction of the fluid channel.

BRIEF DESCRIPTION OF THE DRAWINGS

Further advantages of the invention will be explained in greater detail below with the aid of the figures and on the basis of exemplary embodiments. In the figures.

DETAILED DESCRIPTION OF THE INVENTION

Figure 1:
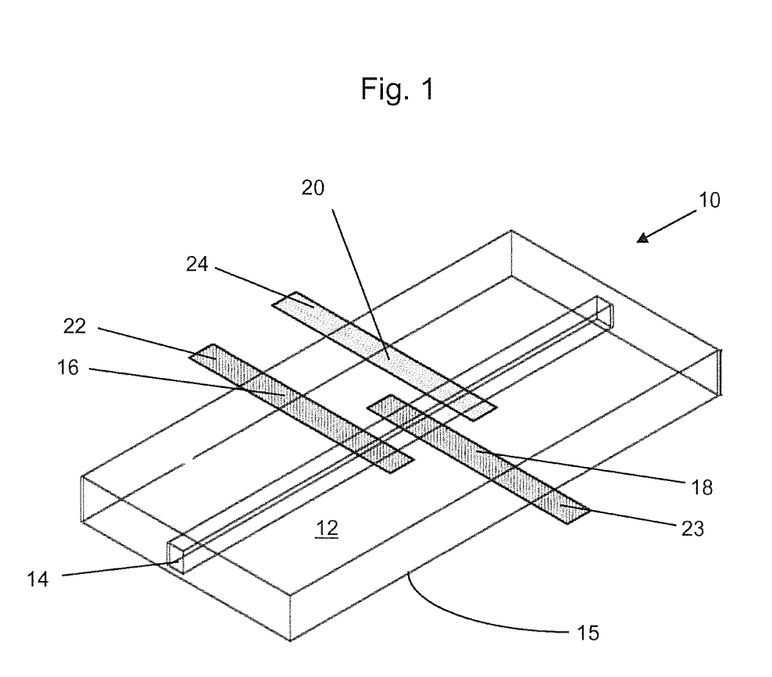
FIG. 1 shows a perspective view of a microfluidic component and of a sensor having a transmitting electrode, a receiving electrode and a first shielding electrode.

FIG. 1 shows part of a microfluidic component 10 consisting of a baseplate and a substrate 12, in the interior of which a fluid channel 14 runs. The microfluidic component 10 has a surface 15 which is arranged substantially parallel to the fluid channel 14 and on which there is arranged a sensor in the form of three electrodes 16, 18 and 20. In the orientation shown, the three electrodes 16, 18 and 20 are therefore located on the underside of the substrate 12 on the same surface 15 and are therefore arranged in a coplanar manner. The electrodes 16, 18 and 20 each have a rectangular, strip-shaped geometry and each extend from an opposite edge of the substrate 12 over the fluid channel, so that they are arranged adjacent to the fluid channel 14. At least in the region below the fluid channel, the electrodes 16, 18 and 20 are arranged parallel and directly adjacent to one another. Provided between the electrodes 16 and 18 on the one hand and between the electrodes 18 and 20 on the other hand is an intermediate space in which exclusively a dielectric is located, so that the electrodes 16 and 18 and 18 and 20 are in each case directly capacitively coupled to one another. The ends 22, 23 and 24 of the electrodes 16, 18 and 20 protruding beyond the sides schematically represent connection points for a voltage source and measurement electronics.

Figure 14:
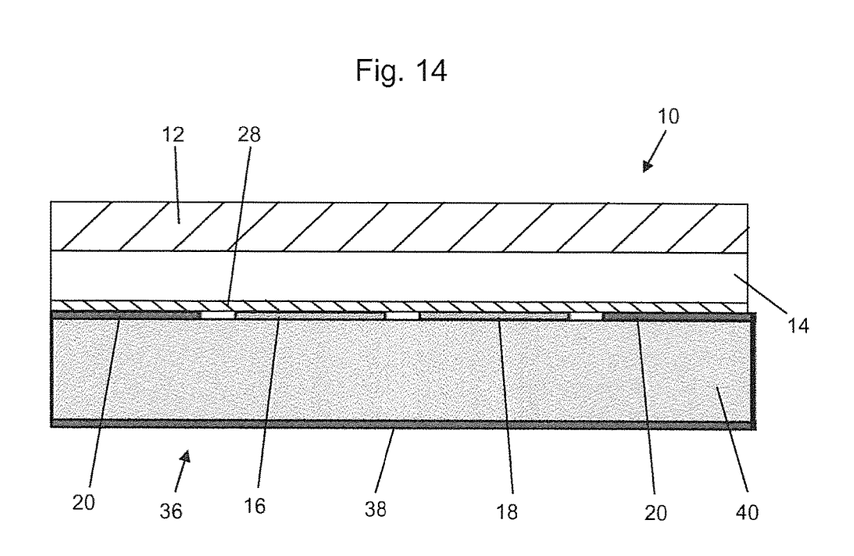
FIG. 14 shows a side view of a second embodiment of the sensor/microfluidic component with second shielding electrode.

In this as in all other diagrams with the exception of FIG. 14, it is deliberately left open as to whether the sensor is configured as an element connected to the microfluidic component 10, that is to say as an integrated sensor, or as an external sensor which is for example part of an operator device, wherein the microfluidic component for measurement purposes is arranged in the illustrated position relative to the sensor. The principle of action on which the invention is based and which will be explained below is the same in both scenarios.

It is also noted that FIG. 1 shows only a schematic partial view of a microfluidic component without further functional elements of typical microfluidic chips, but these are of no significance in the present case. The diagram of the microfluidic component is also simplified to the effect that the cover film typically applied for sealing purposes on one side of the substrate is not clearly shown.

FIGS. 2a, 2b to 5b show a total of eight different electrode arrangements which fall within the scope of the present invention but do not limit the latter. The choice of electrode arrangements shows differences both with regard to the arrangement and also the design of the shielding electrode and with regard to the orientation of the receiving electrode and transmitting electrode relative to the fluid channel 14.

Figure 2A:
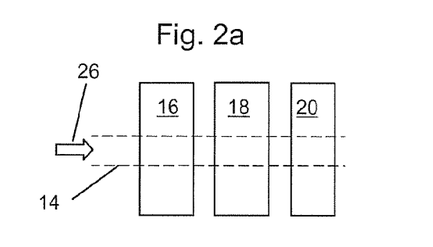
FIGS. 2a, 2b show two first electrode arrangements of the microfluidic component.
Figure 2B:
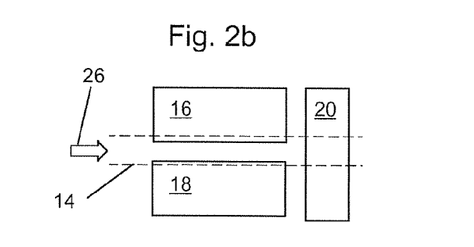

FIGS. 2a and 2b each show electrode arrangements having a transmitting electrode 16, a receiving electrode 18 and a one-piece shielding electrode 20, wherein in both cases the shielding electrode 20, as viewed in the fluid direction denoted by the arrow 26, is arranged behind the transmitting electrode 16 and the receiving electrode 18. FIGS. 2a and 2b differ in that the orientation of the transmitting and receiving electrodes is rotated through 90°. While in FIG. 2a the gap located between the parallel, adjacently arranged edges of the transmitting and receiving electrodes is oriented perpendicular to the fluid channel 14, in the embodiment shown in FIG. 2b it is parallel to the fluid channel 14 and is centered above or below the latter. Both embodiments result in substantially identical signal curves, as will be further discussed below.

Here, as in all other examples with a perpendicular electrode arrangement, the order in which the transmitting and receiving electrodes are arranged relative to the flow direction 26 is not important, and therefore the considerations also apply in the same way when the order is swapped.

The pack consisting of the transmitting electrode and the receiving electrode will also be referred to below as the "basic electrode arrangement".

Figure 3A:
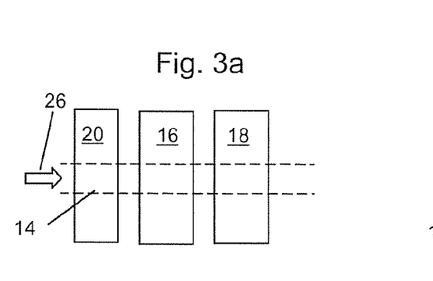
FIGS. 3a, 3b show two second electrode arrangements of the microfluidic component.
Figure 3B:
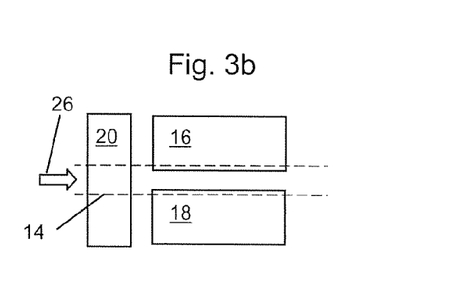

FIGS. 3a and 3b each analogously show a further arrangement of a transmitting electrode 16, a receiving electrode 18 and a one-piece shielding electrode 20. The electrode arrangements differ from those shown in FIGS. 2a and 2b in that in this case the shielding electrode 20, as viewed in the fluid direction 26, is arranged in front of the basic electrode arrangement. In a manner analogous to the exemplary embodiments in FIGS. 2a and 2b, the exemplary embodiments of the electrodes in FIGS. 3a and 3b differ from one another in that the gap between the transmitting electrode 16 and the receiving electrode 18 is oriented in one case perpendicular to the orientation of the fluid channel 14 and in the other case in a parallel and centered manner relative to the orientation of the fluid channel 14.

Figure 4A:
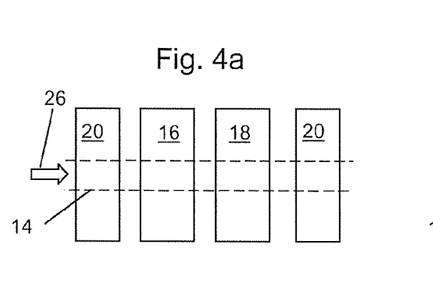
FIGS. 4a, 4b show two third electrode arrangements of the microfluidic component.
Figure 4B:
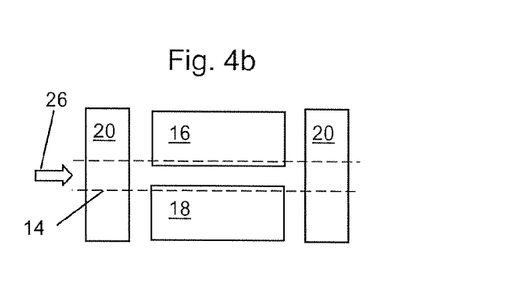

In FIGS. 4a and 4b, the shielding electrode 20 is of two-part design, wherein, with reference to the fluid direction 26, a first part is arranged in front of the basic electrode arrangement and a second part is arranged behind the basic electrode arrangement. The basic electrode arrangement corresponds in each case to the exemplary embodiments shown in FIGS. 4a and 4b described above.

Figure 5A:
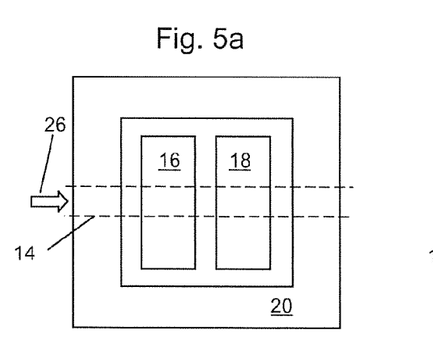
FIGS. 5a, 5b Show two fourth electrode arrangements of the microfluidic component.
Figure 5B:
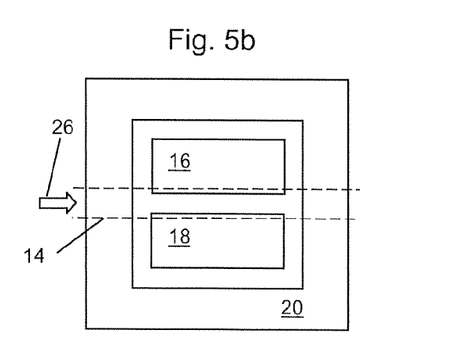

A further electrode arrangement according to the invention is shown in FIGS. 5a and 5b, in which once again the difference is to be seen in the design of the shielding electrode 20. Here, said shielding electrode is in the manner of a frame and completely surrounds the transmitting electrode 16 and the receiving electrode 18. Once again, however, the examples in FIGS. 5a and 5b differ only by the orientation of the gap between the transmitting electrode 16 and the receiving electrode 18.

What all the above-described embodiments of the electrode arrangement have in common is that the shielding electrode 20 is arranged adjacent to the transmitting electrode 16 or to the receiving electrode 18 or to the transmitting electrode 16 and the receiving electrode 18 and spans the fluid channel 14 at least once. It is precisely this fact that ensures a significant signal curve, on the basis of which the position of a liquid front flowing through the fluid channel 14 can be determined.

Figure 6:
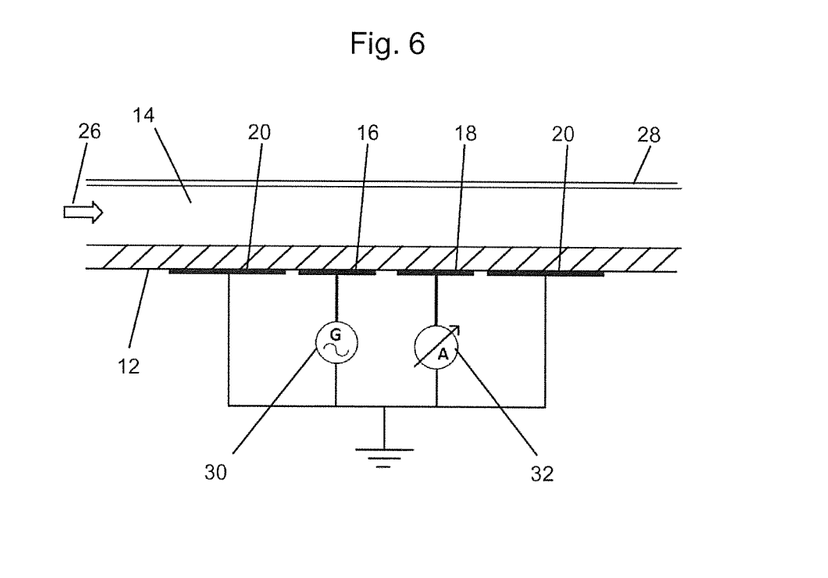
FIG. 6 shows a side view of a first embodiment of the sensor/microfluidic component with circuitry.

FIG. 6 shows a section through a microfluidic component 10 in the region of the fluid channel 14. The microfluidic component has a substrate 12, in which the fluid channel 14 is formed in the manner described above. On its upper side, the substrate 12 is provided with a cover film 28 so that the fluid channel 14 is closed. The fluid direction is again denoted by the arrow 26. Located on the underside of the substrate 12, adjacent to the fluid channel 14, is an electrode arrangement consisting of a transmitting electrode 16, a receiving electrode 18 and a two-part first shielding electrode 20, the first part of which is arranged in front of the transmitting electrode 16 and the second part of which is arranged after the receiving electrode 18, with reference to the fluid direction 26. All the electrodes are located in a plane parallel to or directly on the lower flat surface and are thus arranged in a coplanar manner. Gaps are in each case located between the electrodes so that the receiving electrode 18 is capacitively coupled to the transmitting electrode 16 and the shielding electrode 20 is capacitively coupled both to the transmitting electrode 16 and to the receiving electrode 18. In the illustrated exemplary embodiment, the first shielding electrode 20 is pulled to ground potential. The electrode 16 is connected to an alternating voltage source 30, and the receiving electrode 18 is connected to a signal pickup 32 which is designed to detect the curve of an alternating current signal or alternating voltage signal over time.

Figure 7:
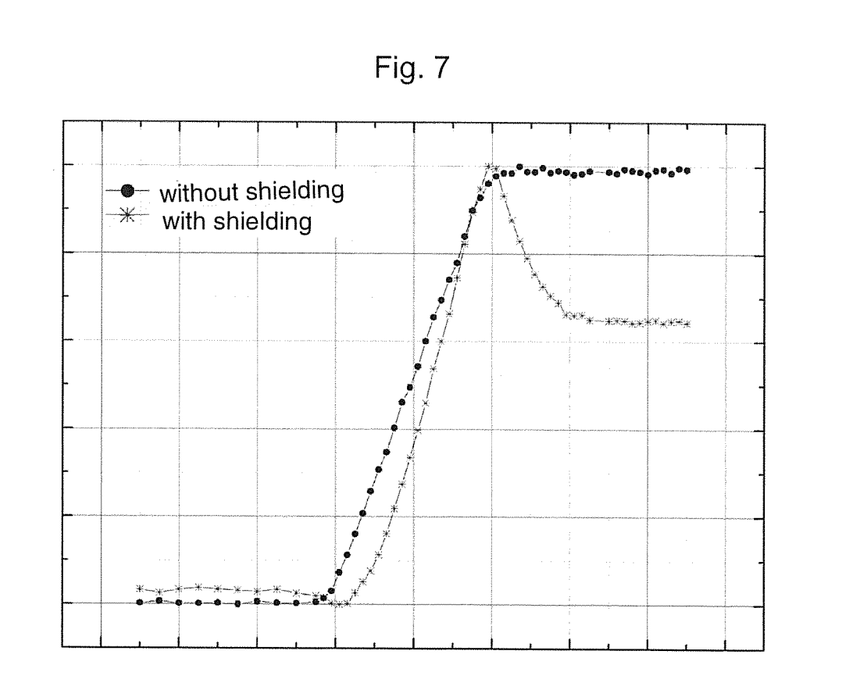
FIG. 7 shows a diagram of a simulation carried out using the sensor according to the invention.

FIG. 7 shows a diagram with two signal curves (simulated), which can each be detected on a receiving electrode. The effective value of the alternating voltage signal or alternating current signal coupled in at the receiving electrode 18 is plotted in the vertical direction, and the time is plotted in the horizontal direction.

The signal curve shown by dots is the signal on a receiving electrode of the basic electrode arrangement without a first and second shielding electrode, which thus does not belong to the subject matter of the present invention. It can be seen that a liquid front passing the basic arrangement generates a significant signal jump, so that even with this basic arrangement the presence of a liquid in the fluid channel in the vicinity of the sensor can in principle be detected. However, information as to where the liquid front is located cannot be read or can be read only very vaguely from the sudden rise alone. This also does not change when a derivation is formed from the dotted signal curve, since the rise in the signal is constant over a relatively broad range.

Seen in comparison to this is the signal curve on an electrode arrangement according to the invention, as shown in FIG. 2a. The electrode arrangement consists of a transmitting electrode 16, a receiving electrode 18 and a first shielding electrode 20, which are arranged in this order one behind the other in the fluid direction 26 and are all three arranged perpendicular to the direction of extension of the fluid channel 14. Merely the presence of the simple first shielding electrode 20 behind the basic electrode arrangement leads to the situation whereby on the one hand the flank of the effective current value or voltage value becomes steeper and a pronounced maximum is obtained at the end of the rise, behind which the effective value drops again to a level that is still increased in comparison to the input value. This formation of an extreme value significantly facilitates the determination of the position of the liquid front since the maximum can easily be determined either directly or in any event by forming the derivation of the measured signal and this extreme value can be assigned to the precise liquid position, as will be explained below.

Figure 8:
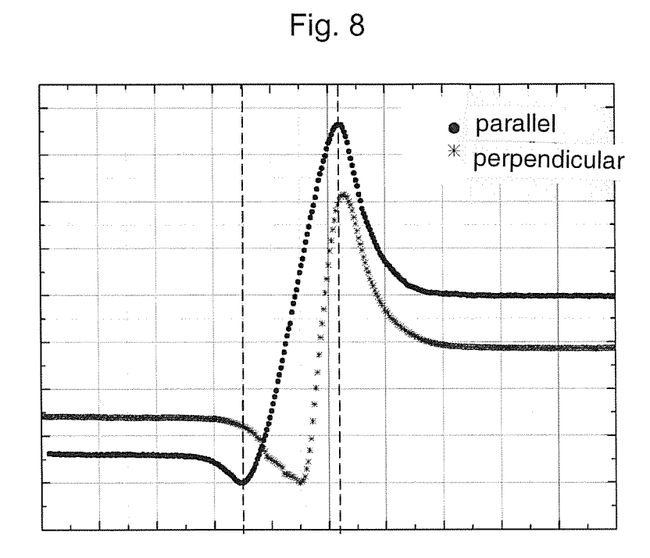
FIG. 8 shows a diagram of two simulations of a sensor according to the invention in different orientation relative to the fluid channel.

However, it will first be shown with reference to FIG. 8 what effect is brought about by the orientation of the gap between the transmitting electrode 16 and the receiving electrode 18 relative to the orientation of the fluid channel 14. The diagram in FIG. 8 shows two signal curves which can be measured using the two electrode arrangements of FIGS. 5a and 5b. Once again, the effective value of the alternating voltage signal or alternating current signal that can be measured on the receiving electrode 18 is plotted in the vertical direction and the time is plotted in the horizontal direction. The result using the electrode arrangement shown in FIG. 5a, in which the transmitting electrode 16 and the receiving electrode 18 are arranged parallel to the fluid channel 14 and are framed by a first shielding electrode 20, is represented by the signal curve shown by dots. The somewhat smaller signal, shown by star-shaped measurement points, was obtained using the electrode arrangement 5b, which differs by the perpendicular orientation of the gap between the transmitting electrode 16 and the receiving electrode 18.

It can clearly be seen that in both curve profiles, in contrast to what is shown in FIG. 7, two extreme values have formed, namely first a less pronounced minimum and then a more pronounced maximum. The two extreme values can be attributed to the fact that the basic electrode arrangement is shielded both on its front side and on its rear side, with reference to the flow direction 26 of the fluid. Therefore it can be seen already at this point that it is not a fundamental difference but rather a qualitative difference that is to be expected if measurements are carried out not using the two electrode arrangements of FIGS. 5a and 5b but rather using those of FIGS. 4a and 4b. In any event, it can be ascertained that both orientations of the basic electrode arrangement are equally suitable for precisely determining the position of the liquid front. The main difference between the two orientations is that slight incorrect positionings lateral to the orientation of the fluid channel are less harmful in the case of a perpendicular orientation than in the case of a parallel orientation. If the gap between the transmitting electrode 16 and the receiving electrode 18 is slightly offset laterally with respect to the fluid channel, a significant weakening of the measurement signal is immediately obtained. A comparable effect in the case of the perpendicular orientation of the transmitting electrode 16 and receiving electrode 18 occurs only with a much greater lateral offset of the entire electrode arrangement with respect to the fluid channel 14.

Based on the two maxima, an even more precise determination of the position of the liquid front can be obtained. Furthermore, the speed at which the liquid or the liquid front is moving in the fluid channel can also be determined.

Figure 9:
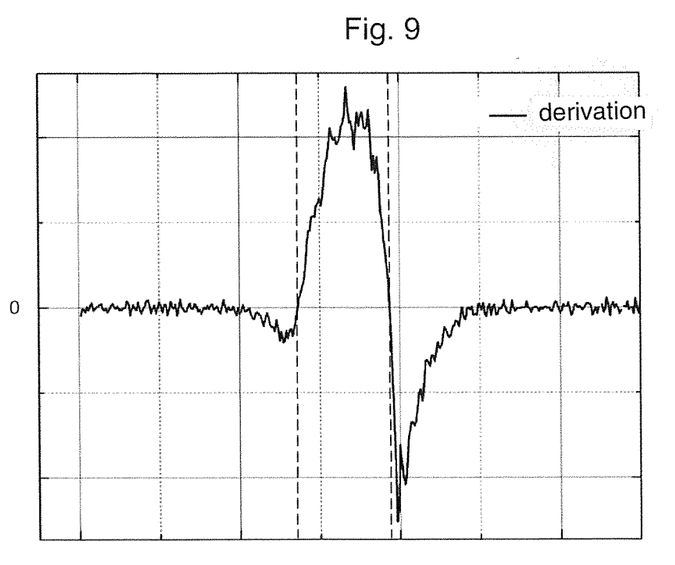
FIG. 9 shows the derivation signal.

For comparison purposes, FIG. 9 shows the derivation signal from the direct signal of the parallel arrangement shown in FIG. 8. The position of the extreme values of the curve of the diagram in FIG. 8 can be determined with greater accuracy from the derivation in FIG. 9 based on the zero crossings which are very sharply pronounced and therefore generate a low reading error.

Figure 10:
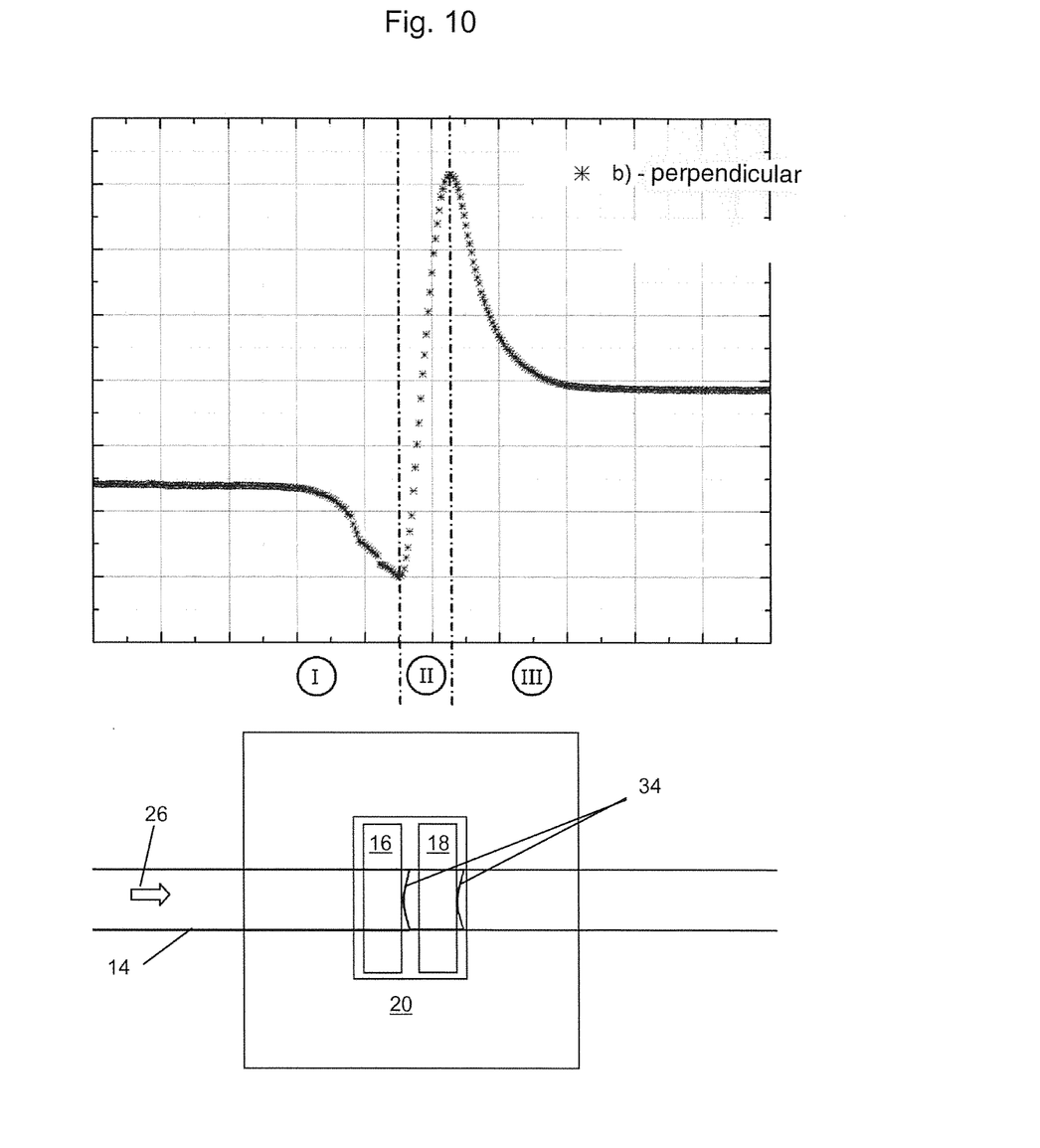
FIG. 10 shows an illustration of the assignment of the extreme values to the position of a liquid front in the fluid channel.

In the top part of FIG. 10, the curve profile already presented in FIG. 8 for a perpendicular arrangement of the basic electrode arrangement is repeated again. Below this in FIG. 10, the associated electrode arrangement is shown schematically. The flow direction of the liquid is again marked therein by the arrow 26. The electrode arrangement is scaled and oriented in such a way that the extreme values of the measurement curve respectively coincide with a gap between the transmitting electrode and the receiving electrode and a gap between the receiving electrode and the shielding electrode. This is intended to illustrate that the extreme values correspond to a snapshot in which the liquid front 34, shown as an arc, has arrived first in one and then in the other gap. It can be seen that the minimum shown in the diagram represents the position of the fluid front in the gap between the transmitting electrode 16 and the receiving electrode 18, while the maximum represents the position of the fluid front in the gap between the receiving electrode 18 and the shielding electrode 20.

The minima and maxima split the diagram into a section I, in which the liquid front runs toward the middle of the basic electrode arrangement, here the gap between the transmitting electrode and the receiving electrode, a section II, in which the liquid front moves across the second half of the basic electrode arrangement, here the receiving electrode 18, and a section III, in which the liquid front 34 moves outward across the shielding electrode 20, that is to say away from the basic electrode arrangement.

The change in the alternating electric field from one of these sections to the next due to the change in the permittivity as the liquid front 34 advances in the fluid channel 14 will be explained with reference to FIG. 11. Said figure shows the field line pattern at four different points in time. Also shown is the fluid channel 14 with the electrode arrangement located therebelow consisting of the transmitting electrode 16, the receiving electrode 18 and the shielding electrode 20 arranged on both sides. It can be seen that the basic electrode arrangement is oriented perpendicular to the channel.

The point in time illustrated in the top part shows the field pattern in the case of an empty fluid channel. The field builds symmetrically around the transmitting electrode 16.

Figure 11:
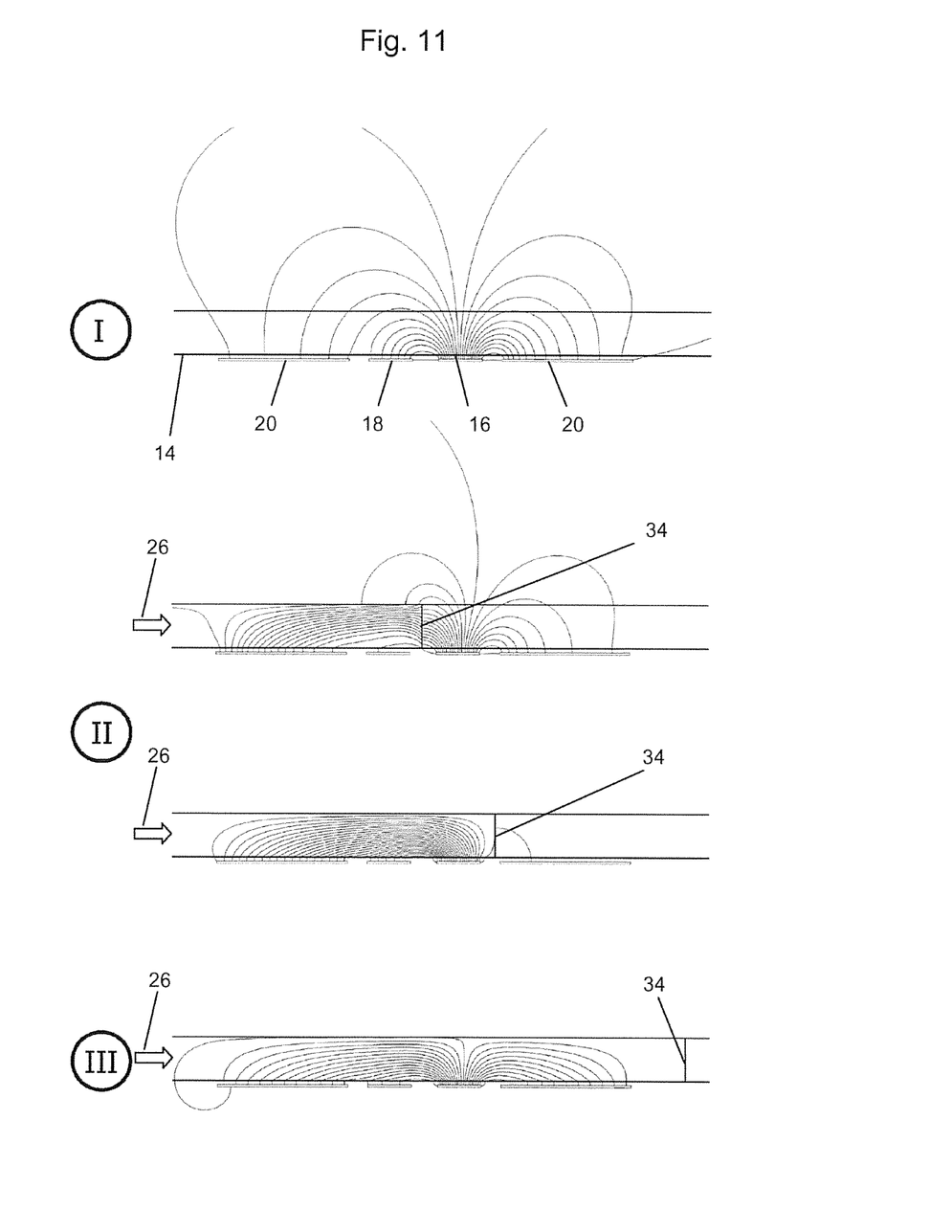
FIG. 11 shows a simulation of the field line distribution for a liquid front advancing in the fluid channel.

The second snapshot in FIG. 11 shows the field pattern while the liquid front 34 is located between the transmitting electrode 16 and the receiving electrode 18. As can be seen, the presence of the liquid in the left-hand channel section ensures that the field lines substantially bridge over the receiving electrode 18 and in a manner of speaking connects the first shielding electrode 20 directly to the transmitting electrode 16. This is the reason for the signal minimum shown at the corresponding location in FIG. 10. The signal therefore drops particularly while the liquid front is moving from the upstream section of the first shielding electrode 20 toward the middle of the basic electrode.

The third snapshot in FIG. 11 shows what happens when the liquid front 34 is located between the transmitting electrode 16 and the downstream section of the first shielding electrode 20. As can be seen, the field lines continue to run from the transmitting electrode 16 to the inlet-side section of the first shielding electrode 20 but also become much denser toward the receiving electrode 18. This ensures the signal maximum shown in the diagram of FIG. 10. The diagram section II, in which the signal rises, is therefore located between the second and third snapshots, while the liquid front is moving from the middle of the basic electrode to the downstream section of the first shielding electrode 20.

Finally, the bottom snapshot in FIG. 11 shows the field pattern when the liquid front 34 has completely passed the electrode arrangement, which corresponds to the signal at the right-hand edge of the image in the diagram shown in FIG. 10. In comparison to the first snapshot, the fact that the field lines run much more densely in the fluid shows that the fluid now present in the fluid channel 14 has a significant effect on the capacitance of the electrode arrangement, which can be attributed to the fact that the permittivity of the fluid is much higher than that of the adjoining medium, for example air. The signal had previously dropped from the maximum value to the increased asymptotic level. The asymptotic level was already substantially reached after the fluid front had completely passed the downstream section of the shielding electrode.

Figure 12:
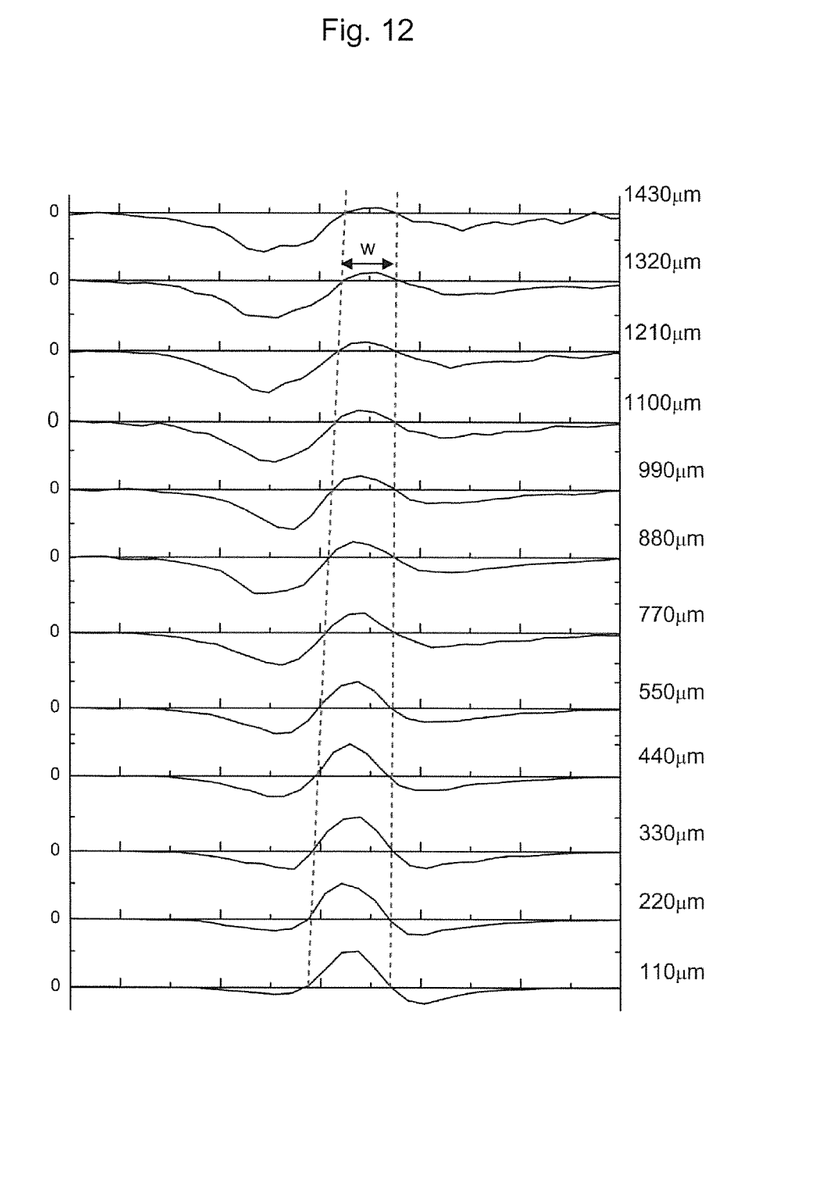
FIG. 12 shows a diagram to illustrate the dependency of the derivation signal on the distance between the electrode arrangement and the fluid channel.

FIG. 12 shows a plurality of different derivation curves as presented in FIG. 9. The zero crossings define in each case the position of the liquid front between the individual sections of the electrode arrangement, as outlined above. Considered from top to bottom, the different derivation curves are based on measurements taken with a decreasing vertical distance between the coplanar electrode arrangement and the fluid channel. As can be seen, the determination of the position of the fluid front is possible for the first time over a wide range of different vertical distances between the electrode arrangement and the fluid channel. The distance varies between 0.11 mm and 1.43 mm and thus by more than 1000%. It can also be seen that the time and thus the position of the zero crossing shifts only slightly backward as the distance between the electrode arrangement and the fluid channel increases, and that also the distance w between the maximum and the minimum changes only moderately. This great tolerance with regard to distance could be seen as a general advantage of the arrangement having a first shielding electrode and thus represents a further advantage of the electrode arrangement according to the invention. In principle, however, it is preferred to arrange the electrode plane as close to the fluid channel as possible, that is to say a distance of at most 0.5 mm and particularly preferably at most 100 μm.

Figure 13:
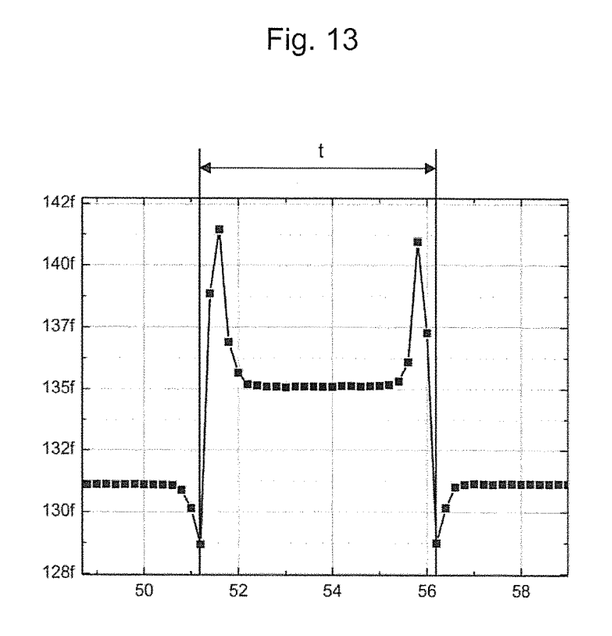
FIG. 13 shows the curve of the signal when passing a liquid column in the fluid channel.

FIG. 13 shows a curve which represents the measurement signal when a finite liquid column (also known as a plug) passes the electrode arrangement. While first the front liquid front as seen in the flow direction, that is to say the interface between a leading medium (air, gas or a liquid having a different permittivity) and the liquid to be detected, passes over the electrode arrangement, the signal rise discussed above and shown on the left-hand side in the diagram of FIG. 13 is obtained, said signal rise having a minimum and a subsequent maximum. After passing over the electrode arrangement, the measurement signal remains at the higher signal until the rear liquid front, that is to say the interface between the liquid and the trailing medium (air, gas) passes over the electrode arrangement. In this case, a mirror-image signal curve is obtained in which the signal curve first has a pronounced maximum and then has a minimum and assumes the smaller initial value again as the rear of the liquid droplet runs out.

From all of the signal curves discussed above having at least one minimum and one maximum, it is possible to determine by simultaneous time measurement not only the position but also the speed at which the liquid droplets have passed over the measurement site.

FIG. 14 shows a section through an embodiment of an external sensor 36 with a microfluidic component 10 placed thereon. As before, the microfluidic component 10 has a substrate 12, in which the fluid channel 14 is formed in the manner described above. On its upper side, the substrate 12 is provided with a cover film 28 so that the fluid channel 14 is closed. Since the microfluidic component 10 is shown here placed upside down on the sensor 36, the upper side thereof therefore points downward. The fluid direction is again denoted by the arrow 26.

This time, the transmitting electrode 16, the receiving electrode 18 and the two-part first shielding electrode 20 are located in the plane parallel to and directly on the upper flat surface of the cover film 28 of the microfluidic component 10. The first part of the first shielding electrode 20 is once again arranged in front of the transmitting electrode 16 and the second part is arranged after the receiving electrode 18, with reference to the fluid direction 26. Gaps are in each case located between the electrodes so that the receiving electrode 18 is capacitively coupled to the transmitting electrode 16 and the shielding electrode 20 is capacitively coupled both to the transmitting electrode 16 and to the receiving electrode 18.

As a further significant difference from the embodiments discussed above and shown in FIG. 6, the sensor 36 here has a second shielding electrode 38 parallel to and at a distance from the plane formed by the transmitting electrode, receiving electrode and first shielding electrode. Specifically, the transmitting electrode 16, the receiving electrode 18 and the first shielding electrode 20 are applied to a first surface and the second shielding electrode 38 is applied to an opposite second surface of a printed circuit board 40. The purpose of the second shielding electrode 38 is to limit the sensitive area of the sensor on the side facing toward the microfluidic component and thus to increase the sensitivity for the permittivity changes taking place there. This design of the external sensor 36 can easily be installed in an operator device (not shown here) for the microfluidic chip 10.

LIST OF REFERENCES 10 microfluidic component
12 baseplate/substrate
14 fluid channel
15 underside
16 transmitting electrode
18 receiving electrode
20 first shielding electrode
22 connection point
23 connection point
24 connection point
26 flow direction
28 cover film
30 alternating voltage supply/signal source
32 signal pickup
34 liquid front
36 external sensor
38 second shielding electrode
40 printed circuit board
b spacing between the extreme values
t distance between liquid front and end of the liquid droplet

What is claimed is:

1. A sensor for detecting a liquid in a fluid channel of a microfluidic component, comprising: an electrode arrangement having a transmitting electrode, a receiving electrode and a first shielding electrode, which are arranged in a coplanar manner on a plane and can be positioned parallel to the fluid channel and above or below adjacent to the fluid channel, wherein no shielding is provided between the transmitting electrode and the receiving electrode so that they each have an adjacently arranged edge with a dielectric located therebetween and so that they are directly capacitively coupled.

2. The sensor according to claim 1, wherein the adjacently arranged edges run parallel.

3. The sensor according to claim 1, wherein the first shielding electrode is capacitively coupled to the transmitting electrode or to the receiving electrode or to the transmitting electrode and the receiving electrode.

4. The sensor according to claim 1, wherein the first shielding electrode is arranged adjacent to the transmitting electrode or to the receiving electrode or to the transmitting electrode and the receiving electrode.

5. The sensor according to claim 4, wherein the first shielding electrode has at least two sections, of which, as viewed in a direction in the plane, a first section is arranged in front of and a second section is arranged behind the transmitting electrode and the receiving electrode.

6. The sensor according to claim 1, wherein the first shielding electrode at least partially frames the transmitting electrode and the receiving electrode in the plane.

7. The sensor according to claim 1, wherein the first shielding electrode is grounded.

8. The sensor according to claim 1, having a signal source, which is connected to the transmitting electrode, and a signal pickup, which is connected to the receiving electrode.

9. The sensor according to claim 8, wherein the signal source is an alternating voltage source.

10. The sensor according to claim 8, wherein the signal pickup is designed to detect a curve of an alternating current signal or alternating voltage signal over time.

11. The sensor according to claim 10, wherein the signal pickup is designed to extract at least one extreme value from the alternating current signal or alternating voltage signal and to output said extreme value(s).

12. The sensor according to claim 1, wherein the electrode arrangement has a second shielding electrode arranged parallel to and at a distance from the plane.

13. The sensor according to claim 12, wherein the second shielding electrode is grounded.

14. A microfluidic component having a surface and a fluid channel running in an interior of the component, substantially parallel to the surface, including a sensor according to claim 1, wherein the transmitting electrode, receiving electrode and first shielding electrode of which are arranged in a coplanar manner on the surface and above or below adjacent to the fluid channel.

15. The microfluidic component according to claim 14, wherein the transmitting electrode and the receiving electrode each have an adjacently arranged edge with a dielectric located therebetween, and the adjacently arranged edges are oriented substantially perpendicular to the fluid channel.

16. The microfluidic component according claim 14, wherein the first shielding electrode is arranged adjacent to the transmitting electrode or to the receiving electrode or to the transmitting electrode and the receiving electrode and spans the fluid channel at least once.

17. The microfluidic component according to claim 14, wherein the first shielding electrode has at least two sections, of which, as viewed in each case in the direction of the fluid channel, a first section is arranged in front of and a second section is arranged behind the transmitting electrode and the receiving electrode.

18. The microfluidic component according to claim 14, wherein the transmitting electrode, receiving electrode and first shielding electrode of the electrode arrangement are arranged at a distance of 500 µm or less, or 100 µm or less, from the fluid channel.

19. The microfluidic component according to claim 14, wherein the electrode arrangement has a second shielding electrode arranged parallel to and at a distance from the surface.

20. A method for detecting a liquid in a fluid channel of a microfluidic component by an electrode arrangement having a transmitting electrode, a receiving electrode and a first shielding electrode, which are arranged in a coplanar manner on a plane substantially parallel to the fluid channel and above or below adjacent to the fluid channel, wherein no shielding is provided between the transmitting electrode and the receiving electrode so that they each have an adjacently arranged edge with a dielectric located therebetween, said method comprising the steps:

applying an alternating voltage to the transmitting electrode, directly coupling the alternating voltage into the receiving electrode, tapping an alternating current signal or alternating voltage signal on the receiving electrode, extracting extreme values from the tapped alternating current signal or alternating voltage signal, assigning the extreme values to the position of a liquid front.

21. The method according to claim 20, wherein the first shielding electrode has at least two sections, of which, as viewed in each case in the direction of the fluid channel, a first section is arranged in front of and a second section is arranged behind the transmitting electrode and the receiving electrode, and in that a speed of the liquid front is derived from at least two temporally successive extreme values.

22. The method according to claim 20, wherein the microfluidic component is positioned with a surface, which runs substantially parallel to the fluid channel, adjacent to the electrode arrangement, which is part of an external sensor having an electrode arrangement having a transmitting electrode, a receiving electrode and a first shielding electrode, which are arranged in a coplanar manner on a plane and can be positioned parallel to the fluid channel and above or below adjacent to the fluid channel, wherein the transmitting electrode and the receiving electrode are capacitively coupled in that they each have an adjacently arranged edge with a dielectric located therebetween, in an operator device.

23. The method according to claim 20, wherein the transmitting electrode and the receiving electrode each have an adjacently arranged edge with a dielectric located therebetween, and the adjacently arranged edges are positioned substantially perpendicular to the fluid channel.

* * * * *